US005824629A

United States Patent [19]
Petritsch

[11] Patent Number: 5,824,629
[45] Date of Patent: Oct. 20, 1998

[54] EFFERVESCENT HAIR CLEANSING AND CARE TABLETS

[76] Inventor: Erich Petritsch, Währinger Strasse 76, Wien A-1090, Austria

[21] Appl. No.: 656,265

[22] PCT Filed: Dec. 12, 1994

[86] PCT No.: PCT/AT94/00194

§ 371 Date: Jun. 26, 1996

§ 102(e) Date: Jun. 26, 1996

[87] PCT Pub. No.: WO95/15745

PCT Pub. Date: Jun. 15, 1995

[51] Int. Cl.⁶ ............... C11D 1/65; C11D 7/12; C11D 7/08

[52] U.S. Cl. ............ 510/120; 510/119; 510/125; 510/127; 510/135; 510/140; 510/141; 510/142; 510/148; 510/156; 510/414; 510/419; 510/424; 510/434; 510/435; 510/439; 510/440; 510/445; 510/446; 510/447; 510/477; 510/478; 510/509

[58] Field of Search ............... 510/119, 120, 510/125, 127, 135, 140, 141, 142, 148, 156, 414, 419, 424, 434, 435, 439, 440, 445, 446, 447, 477, 478, 509

[56] References Cited

U.S. PATENT DOCUMENTS

| | | | |
|---|---|---|---|
| 3,328,307 | 6/1967 | Schmitz | 252/106 |
| 4,253,842 | 3/1981 | Ehrlich | 8/137 |
| 4,592,855 | 6/1986 | Gioffre et al. | 252/89.1 |
| 4,933,100 | 6/1990 | Ramachandran | 252/95 |
| 5,062,994 | 11/1991 | Imperatori | 252/545 |
| 5,110,603 | 5/1992 | Rau | 424/466 |

FOREIGN PATENT DOCUMENTS

| | | | |
|---|---|---|---|
| 253123 | 3/1967 | Austria . | |
| 0 150 250 | 8/1985 | European Pat. Off. | A61K 7/50 |
| 0 330 435 | 8/1989 | European Pat. Off. | A61K 7/075 |
| 0 498 272 A1 | 8/1992 | European Pat. Off. | A61K 7/50 |
| WO 89/03670 | 5/1989 | France | A61K 7/50 |
| 42 00 467 A1 | 7/1993 | Germany | A61K 7/075 |

OTHER PUBLICATIONS

Nowak, G.A., *Die kosmetischen Präparate*, Chapter XXIII, pp. 672–674, Verlag für chen. Industrie H. Ziolkowsky KG—Augsburg.

Ryoji, Tanabe, Japanese Abstract, *Novel Hair Detergent Composition*, Publication No. JP62294604, Publication Date Dec. 22, 1987, vol. 12, No. 191.

Yorozu Hidenori, Japanese Abstract, *Cleaner for Skin or Hair*, Publication No. JP61293908, Publication Date: Dec. 24, 1986, vol. 11, No. 163.

*Primary Examiner*—Paul Lieberman
*Assistant Examiner*—Charles Boyer
*Attorney, Agent, or Firm*—Darby & Darby

[57] ABSTRACT

The invention relates to a hair cleansing and care agent in tablet form, wherein the tablet comprises a base compound which, upon contact with water, sets free a physiologically harmless gas, preferably $CO_2$, and which is formed preferably with a combination of at least one carbonate, possibly carbamate and/or hydrocarbonate, and at least one preferably organic acid in solid form, at least one solid surfactant compatible with hair and skin, at least one additive effective for the care of hair and/or skin, and at least one stabilizer and/or an accessory agent and/or additive for tablets or for the formation of tablets

13 Claims, No Drawings

EFFERVESCENT HAIR CLEANSING AND CARE TABLETS

BACKGROUND OF THE INVENTION

1. Field of the Invention

The invention relates to the field of cleansing and/or care agents, especially for hair, a field which can no longer be imagined to be absent from modern life and which extends from the personal need for health, hygiene and aesthetics to the human-socioeconomic, service and professional cosmetic industry.

In modern life, in the private as well as in the commercial sector, it is very important now and will be even more important in the future that the substances which make up the aforementioned materials and which are, of course, defined more or less by the requirement of compatibility with the human body, are compatible with the environment, especially with respect to their wrapping, packaging, presentation, repackaging as well as their disposal.

Since quite a long time, the hair cleansing and care product industry is dominated without a serious challenging differentiated product by various shampoos for various specific purposes, where these dominating shampoos are always supplied in a highly viscous, liquid-creamy or creamy form with often rather similar functionality.

Every conceivable package variety which packaging technology can supply, is available in a form which is relatively easy to handle, but environmentally not very friendly, starting with single-use packages for a single shampoo or hair care event, where such shampoos and hair care products are packaged in envelopes pads, bags, blister packs and sacks, to a container or bottle with a special closure which is a very effective advertising tool, but very costly to implement; in addition, there is a tendency to package everything, if at all possible, in form of more and more involved, self-contained hair care sets or series. Aside from glass containers, this field is dominated by all different types of plastic materials; the problems associated with the disposal of the large quantities generated by their continuous use, however, need not be discussed at this place.

Because of the magnitude of the aforementioned problems, which at first do not appear serious, but should not be underestimated, it is the object of the invention to reduce and optimize in the hair care industry the extent and specifically the volume of packaging materials in an environmentally responsible fashion, without in any way impeding the ease of handling of the hair care products.

It has been recognized that in order to realize this object in the hair care sector, it would be very advantageous to provide shampoos and hair care products in a compact, solid form, without the unpleasant side effects of handling powders. However, the dispersion and dissolution speed of their active ingredients during hair cleansing and hair care does not always match the expectations of the modern consumer for "instant" availability. Therefore, the general concept of something like a hair shampoo or hair treatment tablet had to be developed which must, however, also offer a system which promotes a rapid dispersal of the ingredients comparable in speed to the dispersal of customary shampoos in wet hair.

2. Background of the Invention

The following comments apply to the present state of the technology for dispersing materials with the aid of gases:

A formed solid bath additive is described in AT-PS 253 123, which, however, does not make reference to a "hair wash" which is rather different from a full bath. This bath additive, which is not identical to a hair cleansing agent, is designed such that the gas is not forming at a time when the material has already come in contact with the bath water; rather, the generation of $CO_2$ already takes place during the fabrication process of the formed solid bath additive and stops before the completion of the production process. The only function of the gas is that of a foaming agent and the gas is already completely embedded into the pores in the surfactant melt. The gas is not capable to advance "crumbling" or mechanical disintegration of the tablet and to disperse its surfactants through a spontaneous evolution of gas activated by an in-situ expansion.

This patent does not contain a suggestion or even an indication for a specific hair care product for cleansing hair.

In EP-A2 330 435, merely a somewhat modified soap is suggested as a solid compact hair cleansing agent, where the soap has a customary shape and is of a customary type, but lacks a dispensing system, which cannot ensure the immediate dispensing of active cleansing surfactants which consumers expect when they wash their hair.

EP-A1 150 250 addresses very generally the dispersion of additives, for example oils, perfume and therapeutic additives in low effective concentrations, in large quantities of water and proposes various types of shapes—but only for the gas emitting system itself, however, without information about and regard for the substances to be dispensed or their quantities which can be quite high in the case of surfactants and soaps. Their properties in particular can be decisive for the effectiveness of such dispersing system. If the compacted components have "lubricating" properties, as is the case for soaps and surfactants, water will be "blocked" from entering the $CO_2$ generating system.

Furthermore, bath additives with a "gas bubbling system" according to the aforementioned BP-A1 do not pertain to the problems associated with hair cleansing, since in a full bath there is a disproportionate quantity of water present as a solvent and time is also not a determining factor.

When shampooing hair, a hair cleansing and care agent (like liquid shampoo) is applied to the palm of the hand and then dispersed in the hair by moving the hand(s) through the wet hair, with the expectation that foam will be formed immediately. This is not very critical for a bath or bubble bath, where plenty of water is available and the water will be bubbling when it enters the bathtub.

Finally, in U.S. Pat. No. 3,328,307, there is described a preparation for a bath using special surfactants which are based on quaternary ammonia compounds with carboxyl groups with an emphasis on a liquid preparation. It is also mentioned therein that solid forms are feasible which can be obtained by mixing these surfactants with base compounds or with thickening agents. In example III of that patent, there is described blending a mixture which is made from solid material obtained by concentrating a liquid preparation of surfactants, with sodium chloride, sodium bicarbonate and tartaric acid as well as pine oil and fluorescein, where the material so obtained is compacted in the form of tablets.

As far as the desired dispersion of surfactants is concerned, it is emphasized in the aforementioned example that the tablets will have to be positioned in a rapidly moving water jet, meaning that they will have to come in contact with a large quantity of water which is flowing rapidly. As a result, this US-A1 was not able to contribute to the development of a new hair cleansing agent in solid form.

SUMMARY OF THE INVENTION

It is therefore the object of the invention to provide a new hair cleansing and/or care agent, especially for human hair, based on at least one surfactant compatible with hair and skin and on additional care additives and accessory agents, characterized in that the cleansing and/or care agent is formed as a solid body, especially in form of a tablet representing a single-use unit or portion, in particular for the purpose of reducing and minimizing packaging and package volume, wherein the solid body is partially compacted and designed to disintegrate spontaneously when manipulated in contact with water, and to break up and/or to disperse and/or to dissolve rapidly when in the liquid phase; said cleansing and/or care agent further based on a mixture or blend of fine and homogeneously dispersed particles, wherein the mixture comprises as essential components a base compound which, upon contact with water, sets free a physiologically harmless gas, preferably $CO_2$, and which is formed preferably with a combination of at least one carbonate, possibly carbamate and/or hydrocarbonate, and at least one preferably organic acid in solid form; the mixture further comprising at least one solid surfactant compatible with hair and skin, at least one additive effective for the care of hair and/or skin, and at least one stabilizer, in particular MgO and/or an alkali-aluminate, and/or an accessory agent and/or additive for tablets or for the formation of tablets.

It is important to point out that the new agent is also capable to cleanse and care for areas on the scalp which are immediately adjacent to or at least close to the hair.

The unexpected result of incorporating a solid phase disintegrating and foaming system which functions independently and only upon contact with water, lies in the fact that the tablet and its ingredients is/are dispersed within a remarkably short time over the entire hair area which is to be treated; this occurs immediately upon the first contact with the wet hair or through a rubbing motion with moist hands, i.e. by manipulative contact, through which the tablet and its ingredients can commence their cleansing action and effect.

The same effect, namely a time-saving and uniform distribution during hair treatment, occurs when the care agent is used in an inventive tablet form; the additional benefit is here the evolution of a nascent gas, a so-called "mineral water refreshing effect", which is regarded as rather pleasant and which is also present in the cleansing tablets.

The new form of the tablets which is environmentally benign, ensures that there is no longer a need for a liquid-proof and pressure-proof package, and even a single-use offer, e.g. 1 tablet for a hair pre-wash and 1 tablet for the main hair wash or a similar arrangement, requires only one simple package for all tablets, e.g. a carton, which can also be realized in the form of a recyclable, refillable, prominently displayed and aesthetically sophisticated and pleasing glass container or a similar container. In addition, using a tablet obviates the disadvantages associated with opening small single-use bags filled with liquid shampoo, like bursting of the bags or the inability to find a piercing or cutting tool for opening the foil of the package.

An example for the aforementioned expression "pseudoalkali" is ammonium and single or multiple alkylated ammonium. The expression in parentheses "(poly-)" cited above refers to "mono-, di-, or poly-."

PREFERRED EMBODIMENTS

As far as the composition of the new solid phase hair cleaning or care agents is concerned, solid materials were especially successful. The agent may have the following composition, based on the total mass of the solid body, in particular of the tablet: Gas-generating base compound system: 35–65%, preferably 40–60%; Surfactant(s): 25–45%, preferably 30–40%; Additive(s): 3–12%, preferably 5–10%; Auxiliary Compound(s), Additive(s), Stabilizers: 1–5%.

The novel cleansing and care tablets having this composition are distinguished in that they disintegrate completely and rapidly in contact with water in liquid form; they withstand, however, an extended time period in an ambient with high relative humidity as can be found in treatment rooms and in bath rooms; the tablets also tend not to stick to each other.

Especially advantageous, as far as the compatibility with hair and skin and the distribution rate during the care process is concerned, are hair care agents with ingredients which promote disintegration and the generation of gas and in which the base compound is formed from a combination of at least one alkali, pseudo-alkali and/or alkaline earth carbonate and/or hydrogen carbonate, especially sodium hydrogen carbonate or magnesium (hydrogen) carbonate, and at least one acid from the group of saturated or unsaturated aliphatic and/or aromatic di- or polycarboxylic acids, (poly) hydroxy-(poly)carboxylic acids and (poly)amino(poly) carboxylic acids, wherein said combination promotes the disintegration of the solid body or the tablet and the distribution of its content through the generation of a gas upon contact with liquid water.

A combination of the components of the base compound which very effectively promotes the distribution of additives and surfactants during the cleansing and care process and which generates a uniform evolution of gas and small gas bubbles, is advantageously provided by shampoo and care tablets. The base compound of the solid body which promotes disintegration and distribution and generates gas, comprises at least one physiologically compatible, organic acid in the solid phase, taken from the group consisting of tartaric acid, citric acid, lactic acid, glutaric acid, fumaric acid, succinic acid and/or malic acid, alanine, valine, leucine or similar, aspartic acid, glutamic acid, salicylic acid, sorbic acid, benzoic acid and/or ascorbic acid.

It was found that the uniformity and effectiveness of the wet distribution of the new hair cleansing and care agent in the hair is optimized under practical conditions, like those occurring at home or in a beauty salon, in the presence of a relative stoichiometric excess of the solid acid component in the base compound which generates the foaming gas and is preferably 25–5%; these conditions also meet the expectations of the consumer. The relative stoichiometric concentration of the acid in the base compound which promotes disintegration, is higher than the concentration of the components in the base compound which generate the gas.

In this context, it is especially advantageous to employ the new solid phase hair agents within an effective pH-range, mainly as protection for hair which is already chemically and mechanically strained as a result of the cleansing process. It is particularly advantageous if the new hair cleansing agents are designed to be approximately pH-neutral or slightly acidic. Thus, the agent has a total pH-value of less than 6.8, preferably between 3 and 6, after the solid bodies or the tablet, as the case may be, have disintegrated or dissolved or are distributed in the aqueous wash and care phase, respectively.

The composition of the new solids items or tablets with respect to their surfactants will preferably be selected, in that its solid body or tablet comprises as surfactant for a predominant cleansing and wash function at least one anionic surfactant in the solid phase, taken from the group consisting of the $C_8$- to $C_{22}$-, preferably of the $C_{12}$- to $C_{20}$-, fatty alcohol esters, preferably sulfates and/or sulfonates, alkyl aryl (benzene) sulfates and/or sulfonates, their alkali (Na, K), earth alkaline (Mg), ammonium salts as well as their mono- and di-ethanol amides, of the customary fatty acid salts (soaps) as well as of the $C_{12}$- to $C_{20}$- fatty acid mono- and/or di-ethanolamides, thio-succinic acid ester, alkyl polyglycol ether sulfates or sulfonates, or a corresponding surfactant mixed with an anionic surfactant. This is, if the new form of hair treatment agents is mainly used more for their wash and cleansing effect, however, without ignoring the positive after-wash regenerating effects.

From the classes of anionic surfactants listed above, the individual anionic surfactant taken from the group of sodium- or magnesium-lauryl- or cetyl-sulfate or sulfonate, cocos fatty acid mono- or di-ethanol amide and (sodium- or magnesium-) cumene sulfate or sulfonate are preferred due to their beneficial long-term effects extending beyond the cleansing process itself.

If the emphasis of the new solid phase agent is less on a separate cleansing effect and more on hair care—and, of course, also on the simultaneous scalp and skin care—, then the best solution are surfactants from the groups of cationic surfactants, such as quaternary ammonium compounds or salts, of dialkyl and trialkyl ammine salts, (especially phosphates or chlorides), preferably alkyltrimethyl-, alkyldimethyl and/or alkylmethyl ammonium salts, (especially chlorides or phosphates).

Again, as is known from extensive experience especially with the chemical base compound responsible for the foam, from this group the individual anionogenic surfactants such as stearyl, lauryl, or cetyl trimethyl ammonium chlorides or phosphates, of distearyl, dilauryl or dicetyl dimethyl ammonium chlorides or phosphates, and of stearyl, lauryl, or cetyl pyridinium chlorides or phosphates, are particularly advantageous.

Hair balsam, hair treatment and hair care tablets perform the basic function to increase the flexibility, the stylability, the fullness, the feel, and the luster of the hair and to maintain or even improve these properties to a significant extent between washes. It is especially important that the scale layer of the hair be closed through proper selection of the pH-value and by supplying nutrients directly, which is equivalent to forming a protective coating on the hair.

The additives for the hair which provide the beneficial effects during the hair cleansing and hair care process, had to be adapted to the major components of the new shampoo and/or hair treatment tablets which comprise the gas generation system and the various surfactants. It is therefore particularly advantageous to incorporate into the new hair cleansing and care agents the classes of additives and the preferred species of additives and anti-irritants compatible with and beneficial for the skin, preferably Allantoin, radical trapping substances, preferably urea, softeners, preferably guarhydroxy propyl trimethyl ammonium chloride, growth promoting additives, preferably Propandiol, dandruff additives, preferably Octopirox, Pyrithione salts, selenium disulfide, anti fat additives, preferably a combination of various (thio) amino acids or isopropyl myristate, fat retarding additives, preferably amino dermine or proteohydrolysates, final treatment additives, preferably silk proteins, dried herb extracts and/or distilled oils or their mixtures.

With respect to the distilled oils which are especially preferred for tablets for the sophisticated consumer because of their care, luster and smell, for example in a beauty salon, as care set, etc., only Ylang—Ylang, sandalwood, cedar, rosewood, bergamot, lavender, balm oil, geranium, patchouli, juniper, peppermint, rosemary, orange, lemon, fennel and mixtures of three or four of the aforementioned oils will be cited as examples.

Dry herb extracts, for example $CO_2$ extracts, are mainly targeted for home use.

More closely related to the surfactants are the auxiliary agents and additives which impact the formation process of the tablets and the stability of the tablets. Their particularly preferred inventive classes and species are, compacting and pressing aids, preferably talcum, fillers, preferably sodium or magnesium sulfate, burst agents, preferably starch, cellulose derivates, carboxy methyl cellulose, alginates, silicon dioxide or titanium dioxide, lubricants and gloss agents, preferably cured castor-oil, metal soaps, etc., dry binders, preferably saccharose, lactose or glucitol, as well as the dyes or colorants, and where the bursting agents which promote the disintegration and hereby the rapid and uniform generation of gas, are of particular importance.

Especially advantageous and environmentally friendly is a presentation in form of single-use packages, each having a volume between 0.5 and 2.5 $cm^3$, preferably between 1 and 1.5 $cm^3$. There are no limitations as far as layout and shapes are concerned.

In order to prevent confusion and mix-ups among the consumers and the distributors and with the idea of creating cleansing and care sets, a colored design can be advantageously and purposely provided such that the solid body is, within the framework of coding or color coding and control system, colored or embossed at least on the surface.

Porosity of the new cleansing and care tablets provides advantageously for their better ability to dissolve, since water which is required for the generation of foam and for the evolution of gas from the basic body, respectively, penetrates the tablet immediately upon contact with wet hair, etc., as a result of capillary action and provides for the gas generation.

For ease of use, for protection of the nasal passages and for ecological reasons, the care tablets may be placed in a dispenser, such as to be positioned within a known tablet dispenser or similar device, which permits a large number of refills.

The fabrication method of the new compact and solid phase shampoos and hair care agents is not significantly different from the known fabrication methods for tablets, where fine particles of solid mixtures are compacted.

If it is planned to add a liquid component, then it is particularly advantageous to engineer the product by intimately mixing the selected components, possibly through additional size reduction, for example through grinding and mixing, metering the resulting mixture and compacting the same under applied pressure to obtain the desired solid body, and, if the addition of a component which exists in liquid phase, like distilled oils, perfumes or Propandiol, is desired, this liquid phase is mixed in a first step with talcum and/or the starch and subsequently introduced into the mixture together with the remaining solid components and finally compacted and pressed into tablets. This is, since a suction effect is employed and, as a result, only solid materials will have to be manufactured into tablets.

EXAMPLE

A charge of 1.8 kg of a starting mixture for a hair cleansing agent in tablet form was prepared using the following components in the following composition:

| | |
|---|---|
| 5% | talcum (DAB), wherein |
| 0.8% | cedar oil are absorbed, |
| 56% | of a 1:1, 1-molar mixture of sodium hydrogen carbonate and lemon oil (all DAB), |
| 33.6% | lauryl sulphonic acid ester-sodium-salt |
| 0.2% | Allentoin |
| 0.5% | Octopirox |
| 1.2% | guano-hydroxypropyl-trimethyl ammonium chloride, and |
| 2% | cornstarch. |

The tablets had a diameter of 1.3 cm and a height of 0.75 cm.

The hair cleansing tablets so obtained tended to dissolve readily in the wet hand accompanied by an immediately evolution of $CO_2$, and during the application and massaging of the tablet into the hair, the content of the tablet dissolved completely within 20 to 25 sec, aided by the gas evolution. The pH-value of the suds so formed was in the neutral-acidic range of around 6.6.

After drying and brushing, the hair exhibited a high luster and firmness and was easy to brush. Since the shampoo tablets were taken from a larger reusable container (glass), no trash was generated.

I claim:

1. A single solid compacted body of cleansing and care agent for human hair, comprising:
   at least one solid surfactant compatible with hair and skin;
   at least one of an additive and an auxiliary compound;
   a base compound which, upon contact with water, sets free a physiologically harmless gas, said base compound being formed from a combination of a least one of a carbonate, carbamate and hydrogen carbonate and at least one organic acid in solid form;
   wherein the cleansing and care agent is provided in the form of cleansing and care units, each unit having a volume of 0.5 to 2.5 $cm^3$, and has the following composition with respect to the total mass of the solid body or tablet:
   Gas-generating base compound system: 40–60%;
   Surfactant(s): 25–45%;
   Additives for hair and scalp care: 3–12%, wherein the additives for hair and scalp care comprise at least one effectual additive for hair and skin care selected from the group consisting of anti-irritants, radical trapping substances, trimethyl ammonium chloride, growth promoters, Pyrithione salts, selenium disulfide, anti fat additives, fat retarding additives, and final treatment additives;
   Auxiliary compounds and additives: 1–5%, wherein the auxiliary compounds and additives are selected from the group consisting of magnesium oxide, alkali aluminate, distilled oils, talcums, sodium or magnesium sulfate, starch, cellulose derivates, carboxy methyl cellulose, alginates, silicon dioxide, titanium dioxide, cured castor-oil, metal soaps, gloss agents, dry saccharose, lactose, glucitol and dyes or colorants, and wherein the relative stoichiometric concentration of the acid in the base compound which promotes disintegration, is higher than the concentration of the components in the base compound which generate the gas, and wherein the cleansing and care agent has a total pH-value of less than 6.8, after the solid bodies or the tablet have disintegrated or dissolved or are distributed in the aqueous phase.

2. The cleansing and care agent according to claim 1 wherein the cleansing agent has the following composition with respect to the total mass of the solid body or tablet:
   Surfactants: 30–40%;
   Additives for hair and scalp care: 5–10%.

3. The cleansing and care agent according to claim 2, wherein the solid body comprises as surfactant at least one physiologically harmless, cationic surfactant in solid form from the group consisting of quaternary ammonium compounds and salts, dialkyl and trialkyl ammine salts, alkyldimethyl and alkylmethyl ammonium salts, chlorides or phosphates.

4. The cleansing and care agent according to claim 3, further comprising as cationic surfactant at least one of a surfactant taken from the group consisting of stearyl, lauryl, or cetyl trimethyl ammonium chlorides and phosphates, distearyl, dilauryl or dicetyl dimethyl ammonium chlorides and phosphates, and stearyl, lauryl, or cetyl pyridinium chlorides or phosphates.

5. The cleansing and care agent according to claim 4, wherein the solid body comprises pores.

6. The cleansing and care agent according to claim 1, wherein the solid body is coded by at least one of a color code and embossed on the surface.

7. The cleansing and care agent according to claim 1, wherein the base compound is formed from a combination of at least one of an alkali, pseudo-alkali and alkaline earth carbonate and hydrogen carbonate, and at least one of acid from the group of saturated or unsaturated aliphatic and aromatic di- or polycarboxylic acids, (poly)hydroxy-(poly)carboxylic acids and (poly)amino(poly)carboxylic acids, wherein said combination promotes the disintegration of the solid body or the tablet and the distribution of the content through the generation of $CO_2$ gas upon contact with water.

8. The cleansing and care agent according to claim 1, wherein the base compound of the solid body which promotes disintegration and distribution and generates gas, comprises at least one physiologically compatible, organic acid in the solid phase, taken from the group consisting of tartaric acid, citric acid, lactic acid, glutaric acid, fumaric acid, succinic acid, malic acid, alanine, valine, leucine, aspartic acid, glutamic acid, salicylic acid, sorbic acid, benzoic acid and ascorbic acid.

9. The cleansing and care agent according to claim 1, wherein the solid body comprises as surfactant for a predominant cleansing and wash function at least one anionic surfactant in the solid phase, taken from the group consisting of the $C_8$- to $C_{22}$- fatty alcohol sulfates and sulfonates, alkyl aryl (benzene) sulfates and sulfonates, their alkali (Na, K), earth alkaline (Mg), ammonium salts and their mono- and di-ethanol amides, of the customary soaps as well as of the $C_{12}$- to $C_{20}$- fatty acid mono- and di-ethanolamides, thiosuccinic acid ester, alkyl polyglycol ether sulfates or sulfonates.

10. The cleansing and care agent according to claim 9, further comprising as an anionic surfactant at least one surfactant taken from the group consisting of (sodium- or magnesium-) lauryl- or cetyl-sulfate or sulfonate, cocos fatty acid mono- or di-ethanol amide and (sodium- or magnesium-) cumene sulfate or sulfonate.

11. The cleansing and care agent according to claim 1, wherein the solid body forming said agent is positioned within a tablet dispenser, for permitting refills.

12. A process for making a solid body of hair cleansing and care agents comprising the steps of:
   intimately mixing:
      at least one solid surfactant compatible with hair and skin, and
      at least one of an additive and an auxiliary compound, and a base compound which, upon contact with water, releases a physiologically harmless gas, said base compound comprising at least one of a carbonate, carbamate and hydrogen carbonate, and at least one organic acid in solid form; and forming a cleansing and care agent in the form of a solid body having a volume of 0.5 to 2.5 cm$^3$;

wherein the cleansing and care agent having the following composition with respect to the total mass of the solid body:

Gas-generating base compound system: 40–60%;

Surfactant(s): 25–45%;

Additives for hair and scalp care: 3–12%, wherein the additives for hair and scalp are selected from the group consisting of anti-irritants, radical trapping substances, trimethyl ammonium chloride, growth promoters, Pytrithione salts, selenium disulfide, anti-fat-additives, fat retarding additives and final treatment additives;

Auxiliar compounds and additives: 1–5%. wherein the auxiliary compounds and additives are selected from the group consisting of magnesium oxide, alkali aluminate, distilled oil, talcum, sodium or magnesium sulfate, starch, cellulose derivates, carboxy methyl cellulose, alginates, silicon dioxide, titanium dioxide, cured castor-oil, metal soap lubricants, gloss agents, dry saccharose, lactose, glucitol dry binders, and dyes or colorants, wherein the relative stoichiometric concentration of the acid in the base compound which promotes disintegration is higher than the concentration of the components in the base compound which generate the gas; and wherein the cleansing and care agent has a total pH-value of less than 6.8 after the solid body has disintegrated or dissolved or is distributed in the aqueous phase.

13. A solid compacted body of cleansing and care agent for human hair, comprising:

at least one solid surfactant compatible with hair and skin;

at least one of an additive and an auxiliary compound;

a base compound which, upon contact with water, releases a physiologically harmless gas, said base compound comprising at least one of a carbonate, carbamate and hydrogen carbonate, and at least one organic acid in solid form;

wherein the solid body of cleansing and care agent has a volume of 0.5 to 2.5 cm$^3$, and the cleansing and care agent has the following composition with respect to the total mass of the solid body:

Gas-generating base compound system: 40–60%;

Surfactant(s): 25–45%;

Additives for hair and scalp care: 3–12%, wherein the additives for hair and scalp are selected from the group consisting of anti-irritants, radical trapping substances, trimethyl ammonium chloride, growth promoters, Pyrithione salts, selenium disulfide, anti-fat-additives, fat retarding additives and final treatment additives;

Auxiliary compounds and additives: 1–5%, wherein the auxiliary compounds and additives are selected from the group consisting of magnesium oxide, alkali aluminate, distilled oil, talcum, sodium or magnesium sulfate, starch, cellulose derivates, carboxy methyl cellulose, alginates, silicon dioxide, titanium dioxide, cured castor-oil, metal soap lubricants, gloss agents, dry saccharose, lactose, glucitol dry binders, and dyes or colorants, wherein the relative stoichiometric concentration of the acid in the base compound which promotes disintegration is higher than the concentration of the components in the base compound which generate the gas; and wherein the cleansing and care agent has a total pH-value of less than 6.8 after the solid body has disintegrated or dissolved or is distributed in the aqueous phase.

* * * * *

UNITED STATES PATENT AND TRADEMARK OFFICE
CERTIFICATE OF CORRECTION

PATENT NO. : 5,824,629
DATED : October 20, 1998
INVENTOR(S) : Erich PETRITSCH

It is certified that error appears in the above-identified patent and that said Letters Patent is hereby corrected as shown below:

On the title page, item [30] insert the following:
Item [30] Foreign Application Priority Data Dec. 10, 1993 [AT] Austria - ....... 2501/93---.

Signed and Sealed this

Twenty-second Day of June, 1999

Attest:

Q. TODD DICKINSON

Attesting Officer

Acting Commissioner of Patents and Trademarks